United States Patent [19]

Witonsky et al.

[11] Patent Number: 4,643,980
[45] Date of Patent: * Feb. 17, 1987

[54] GLUTARALDEHYDE INDICATOR

[75] Inventors: Robert J. Witonsky, Princeton; Raymond P. Larsson, Denville, both of N.J.

[73] Assignee: Info-Chem, Inc., Fairfield, N.J.

[*] Notice: The portion of the term of this patent subsequent to Jun. 4, 2002 has been disclaimed.

[21] Appl. No.: 701,388

[22] Filed: Feb. 14, 1985

Related U.S. Application Data

[62] Division of Ser. No. 503,892, Jun. 13, 1983, Pat. No. 4,521,376.

[51] Int. Cl.$^4$ .................... G01N 21/78; G01N 31/22
[52] U.S. Cl. .................................... 436/128; 422/56
[58] Field of Search .................. 422/36, 55, 56, 57, 422/58; 436/1, 128, 169, 130; 116/206

[56] References Cited

U.S. PATENT DOCUMENTS

| | | | |
|---|---|---|---|
| 3,945,798 | 3/1976 | Young | 422/56 |
| 3,960,895 | 6/1976 | Rosenberger et al. | 549/395 |
| 4,075,321 | 2/1978 | Relyveld | 424/92 |
| 4,173,515 | 11/1979 | Aldridge et al. | 435/28 |
| 4,308,028 | 12/1981 | Elkins | 422/58 |
| 4,328,182 | 5/1982 | Blake | 422/56 |

FOREIGN PATENT DOCUMENTS 2085583  4/1982  United Kingdom ............ 436/128

Primary Examiner—Arnold Turk
Attorney, Agent, or Firm—Anthony Lagani, Jr.

[57] ABSTRACT

An indicator capable of determining whether the concentration of a disinfectant/sterilant solution of glutaraldehyde exceeds a predetermined value comprising an indicator medium impregnated with a sulfite compound and an amino acid or an ammonium salt.

16 Claims, 1 Drawing Figure

GLUTARALDEHYDE INDICATOR

CROSS-REFERENCE TO RELATED APPLICATIONS

This application is a division of application Ser. No. 503,892, filed June 13, 1983, now U.S. Pat. No. 4,521,376.

BACKGROUND OF THE INVENTION

While the most widely used method of sterilization in hospitals is steam sterilization, this method is not always practical, because of adverse effects on materials to be sterilized. The long turn around time required for ethylene oxide sterilization often makes this alternative method not practical. A rapid, low temperature method for disinfecting and sterilizing surgical items relies on the use of an alkaline glutaraldehyde solution ("AGS") as the disinfectant/sterilant. The solution is generally used at a 2% concentration.

Studies indicate that the pH of the AGS solution affects both its stability and its biocidal activity. At an acid pH of about 3–4, glutaraldehyde solutions are stable for a period of about two years. However, at low pH levels, AGS does not exhibit exceptional sporicidal activity. The alkalinization of AGS on the other hand, while it optimizes antimicrobial activity, as well as sporicidal activity, promotes an aldehyde polymerization reaction which results in a gradual loss of antimicrobial activity of the AGS.

AGS is considered biocidally active above one percent aldehyde concentration. As a result of alkalination an AGS solution having an initial glutaraldehyde concentration of 2.1% at a pH of 8.5 will degrade over a period of about 28 days at ambient temperatures to a concentration of about 1.3% glutaraldehyde with a concommitant decrease in pH to about 7.4. This chemical degradation limits the useful life of buffered glutaraldehyde to 14 to 28 days depending on the nature and concentration of the buffering agent.

Commercially, AGS is usually supplied at a glutaraldehyde concentration of 2%. To insure effectiveness suppliers advise customers of the effective life of the product, after which time it is recommended that the AGS be discarded. Illustrative of these commercial products and their recommended useful lives are the 2% GA shown in Table I.

TABLE I

| Product 2% Glutaraldehyde (Trademark) | pH | Recommended Useful Life (Days) |
|---|---|---|
| CIDEX | 7.8 | 14 |
| CIDEX 7 | 7.9 | 28 |
| Glutarex | 7.6 | 28 |
| *Wavicide | 6.2 | 28 |

*unbuffered

Since excessive organic loads (blood, pus, mucus, etc.) reduce the effectiveness of AGS, and reuse results in dilution of the solution as a result of rinse water brought in with instruments and AGS removed upon removal of the instruments, time alone is not necessarily determinative of the degree of degradation of an AGS. The effect of these factors on AGS use life cannot be directly expressed quantitatively since the pertinent parameters are not readily measurable. Consequently, in order to insure that the AGS is effective, hospital staff may discard AGS well before the end of the recommended use life. It is known, however, that to obtain kill in all samples of micro-organisms and viruses the lowest concentration of glutaraldehyde which is effective is 1%.

All of the official methods for determining the effectiveness of disinfectants which have been established by the Association of Official Analytical Chemists are complex, time consuming and beyond the technical capabilities of and time constraints on the nusing staffs which use AGS. A new effectiveness test for a particular brand of AGS, Cidex 7, was introduced into commercial distribution recently by Surgikos, Inc. The test method involves the use of a "kit" with a seven step procedure which includes the exact measurement of two reagents, the careful measurement of two others, and a color comparison for determining concentration. A blue color is obtained when the glutaraldehyde concentration falls to 1% or below, and is to be interpreted as the time to replace the AGS. While this test is effective, the industry has long sought a simple "go-no go" test which can be carried out quickly without any need for special care or skill by the operator. Heretofore, no such test has been available.

SUMMARY OF INVENTION

An indicator for determining the effectiveness of a glutaraldehyde sterilant comprising an absorbant medium which has been impregnated with a solution of sulfite compound and an amino acid or ammonium salt. The preferred sulfite is sodium sulfite. The preferred molar ratio of sulfite to amino acid is about 2.5/1 to 20/1. Glycine is the preferred amino acid.

BRIEF DESCRIPTION OF DRAWING

FIGURE—The FIGURE depicts the preferred embodiment of the indicator of this invention.

DETAILED DESCRIPTION

Figure 1:
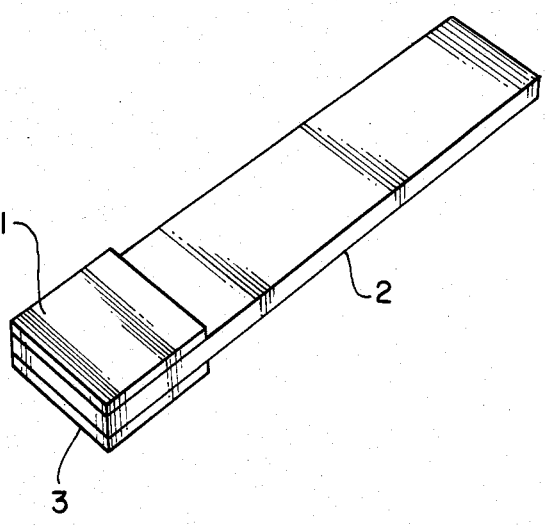

This invention relates to an indicator for measuring the effectiveness of a glutaraldehyde sterilant. More specifically it relates to an indicator which is capable of differentiating between a 2% solution of glutaraldehyde and solutions of lower concentrations. The glutaraldehyde disinfectants are generally alkalinated glutaraldehyde solutions. While unbuffered glutaraldehyde solutions are sterilants and within the scope of this invention, they are not preferred since they tend to initiate rusting of instruments immersed in these solutions.

In its preferred embodiment the indicator of this invention comprises an absorbant medium which has been impregnated with a solution of sulfite compound and an amino acid. While a broad range of sulfite to amino acid ratios can be used, the actual ratio will depend on the particular glutaraldehyde solution and the level at which differentiation between solutions of different concentrations is desired. A preferred ratio is 10/1, more preferably 5/1.

The sulfite/amino acid ratio is not in itself determinative. Too little amino acid available in the glutaraldehyde solution results in a lack of differentiation between solutions of different concentrations. On the other hand, an excess of amino acid results in what is believed to be over-buffering of the indicator making it unresponsive to any concentration of glutaraldehyde in a practical time period; i.e., less than ten minutes.

The indicator can be mounted on any suitable backing strip e.g. plastic, metal foil, paper, etc. The indicator medium is preferably made of an absorbant paper; e.g., chromotography paper. However, any water wettable absorbant material may be used; e.g., polyester fabric, non-woven nylon felt, Tyvek ®, spun bonded polypropylene etc. Alternately, the indicator medium may be an integral part of an absorbant medium at least one end of which has been impregnated with the impregnating solution. A preferred material for the indicator medium is chromotography paper; e.g. S & S 410.

While of course an indicator medium in the form of a small pad may be dipped into the AGS to be tested using a tweezer or other means for holding the pad securely, in its preferred embodiment the pad is adhered to a backing strip.

Depending upon the ratio of sulfite to amino acid and the concentration of amino acid the devices of this invention are responsive to glutaraldehyde concentrations as low as 0.75%. Hence, the indicator can be adjusted to readily distinguish between solutions of glutaraldehyde having concentrations in the 1-2% range. Such an indicator permits hospital nursing staff to confirm that an AGS being used is at an effective concentration.

In its preferred embodiment the indicator of this invention is used to distinguish between 1% and 2% concentration of glutaraldehyde solutions. When dipped into a 2% solution of AGA a yellow color appears on the indicator pad, When the AGS solution has a concentration of 1% or less of glutaraldehyde no color change is observed. Color change appears with solutions between 1% and 2% glutaraldehyde. Hence, the indicator is specific for a 1% concentration and permits hospital staff to know when replacement of AGS solutions must be made by a simple test technique. For this particular device the impregnating solution of choice comprises a one molar solution of sodium sulfite and 0.2 molar amino acid. The preferred amino acids are glycine and lysine.

Tha advantages of the instant invention may be more readily appreciated by reference to the following example.

EXAMPLE I

Solutions of sodium sulfite and amino acids were prepared and tested to determine whether a color change capable of differentiation between a 1% and 2% AGS was discernable. In each case a water solution of 1.0M sodium sulfite and 0.2M amino acid was prepared. Two cubic centimeters of the solution was added to about 20 cc of 2% AGS (Cidex 7). The results are tabulated below.

TABLE II

| Amino Acid | Observation |
|---|---|
| Alanine | N.C.* |
| Arginine | N.C. |
| D,L-Aspergine | N.C. |
| Glutamine | N.C. |
| Glycine | 1 min. some yellow |
|  | 3 min. intense yellow |

TABLE II-continued

| Amino Acid | Observation |
|---|---|
| Leucine | N.C |
| Lysine | 1 min. some yellow |
|  | 3 min. some yellow |

*N.C. = no color change was observed after 24 hour of standing.

EXAMPLE II

Example I was repeated using substituting para-aminobenzoic acid and trihydroxy ammonium methane for the amino acid. No color change was observed in each case.

EXAMPLE III

Example I was repeated using glycine and lysine at 0.1M, 0.2 and 0.3M the results are tabulated below for both a 1% and 2% AGS(CIDEX-7).

TABLE III

| Amino Acid | Amino Acid Concentration | AGS Concentration | Observation |
|---|---|---|---|
| glycine | 0.1 | 1% | some yellow |
|  | 0.1 | 2% | some yellow |
|  | 0.2 | 1% | N.C. |
|  | 0.2 | 2% | intense yellow |
|  | 0.3 | 1% | N.C. |
|  | 0.3 | 2% | N.C. |
| lysine | 0.1 | 1% | N.C. |
|  | 0.1 | 2% | N.C. |
|  | 0.2 | 1% | N.C. |
|  | 0.2 | 2% | some yellow |
|  | 0.3 | 1% | yellow-orange |
|  | 0.3 | 2% | yellow-orange |

At the 0.2M concentration both glycine and lysine were effective to differentiate between a 1% and 2% solution of AGS.

EXAMPLE IV

A water solution of 1.0M sodium sulfite and 0.2M glycine was prepared. Strips of chromatography paper were saturated with the solution and air dried. The dried strips were dipped into test solutions of AGS, immediately removed and allowed to dry. Strips immersed in a 1% AGS showed no color change. Strips immersed in a 2% AGS showed an intense yellow color change in about two minutes.

EXAMPLE V

In order to determine the effectiveness of various concentrations and ratios of sulfite to amino acid, a series of tests were performed in the manner of Example IV. In each case the sulfite and glycine levels were varied. The test strips were evaluated by immersion into solutions of CIDEX 7 and CIDEX of different concentrations of glutaraladehyde. The results are shown in Table IV. The following designations as used in Table IV have the specified meaning.

NR=no response in one hour
SY=strong yellow color
WY=weak yellow color

TABLE IV

| Run No. | A | B | C | D | E | F |
|---|---|---|---|---|---|---|
| $Na_2SO_3$[1] | 2.0 M | 2.0 M | 2.0 M | 0.5 M | 0.5 M | 1.0 M |
| glycine | 0.4 M | 0.2 M | 0.1 M | 0.2 M | 0.1 M | 0.2 M |
| Glutaraldehyde Concentration (%) |  |  |  |  |  |  |
| 2 | NR/NR[2] | SY/SY | SY/WY | SY/SY | SY/SY | SY/SY |

TABLE IV-continued

| Run No. | A | B | C | D | E | F |
|---|---|---|---|---|---|---|
| 1.75 | NR/NR | SY/WY | SY/WY | SY/WY | SY/SY | SY/SY |
| 1.5 | NR/NR | WY/WY | SY/WY | WY/WY | SY/SY | WY/WY |
| 1.25 | NR/NR | NR/WY | SY/WY | WY/NR | SY/WY | WY/WY |
| 1.0 | NR/NR | NR/NR | SY/WY | NR/NR | SY/WY | NR/WY |
| 0.75 | NR/NR | NR/NR | WY/NR | NR/NR | WY/WY | NR/NR |

[1] Concentration of Na$_2$SO$_3$ and glycine in the impregnation solution used to prepare the indicator. The paper used is chromotographcy paper.
[2] The designations show the response for the indicator in CIDEX-7 and CIDEX solutions. The designation before the slash mark (/) is the response for CIDEX 7 while the designation after the slash is for CIDEX. CIDEX is a trademark of Surgikos, Inc. for glutaraldehyde solutions used as sterilants/disinfectants.

As will be seen from the data where the concentration of amino acid in the impregnating solutions is 0.4M the indicator is unresponsive to solutions of glutaraldehyde of 2% or less concentration. At 0.1M amino acid, however, the indicator is generally unresponsive, though differentiation is less precise than 0.2M solutions. At 0.2M amino acid concentration the indicator readily distinguishes between varying concentrations of glutaraldehyde solution. This system is effective at sulfite to amino acid ratios of about 2.5/1 to about 20/1. Hence, the concentration of amino acid in the impregnating solution which will give a response capable of differentiating between glutaraldehyde solutions of different concentrations is about 0.1M to about 0.3M preferably 0.15M to about 2.5M more preferably about 0.18M to about 2.2M, e.g. 0.2M.

EXAMPLE VI

In order to determine whether other organic amines are useful in the practice of this invention, various amines were tested in the manner of Example I at 1M Na$_2$SO$_3$ and 0.2M amine. The response time at 1 hour was noted.

TABLE V

| Amine | Responses (1 hr) |
|---|---|
| Ortho-Aminophenol | N.R. |
| hexamethylene tetramine | N.R. |
| melamine | N.R. |
| dimethyl glyoxime | N.R. |
| 2-amino-2-hydroxymethyl, 1-3, propane diol | N.R |
| trimethyl amine | N.R. |
| 2-2', dipryidylamine | N.R. |
| diphenylamine | N.R. |

It is concluded that amines per se are not operative in the practice of this invention.

EXAMPLE VII

The experiments of Example IV were repeated substituting various ammonium compounds for the glycine. The results obtained with a 2% glutaraldehyde solution are shown in Table VI.

TABLE VI

| Ammonium compound | Response |
|---|---|
| ammonium chloride | slight yellow- 3 min. |
| ammonium acetate | slight yellow- 3 min. |
| ammonium formate | slight yellow- 3 min. |
| ammonium bromide | slight yellow- 3 min. |
| ammonium bicarbonate | slight yellow- 3 min. |

Hence, it is evident that ammonium compounds are effective substitutes for the amino acids of this invention. As used in the specification and claims, the term "ammonium compound" means ammonium salts of organic and inorganic compounds.

While the invention has been described in terms of sodium sulfite, any water soluble sulfite salt is effective. The preferred sulfite compounds are alkali metal sulfites and quarternary ammonium sulfites. Illustrative non limiting examples of such sulfites are sodium sulfite, potassium sulfite, lithium sulfite, tetra methyl ammonium sulfite and trimethyl benzyl ammonium sulfite.

As used in the specification and claims the term "impregnate" means to saturate with a solution and subsequently dry the medium which has been saturated.

While in the case of the absorbant medium of this invention, the sulfites and amino acids as well as ammonium compounds are present on the absorbant medium as dry compounds, these amounts can be quantified with references to the solution from which they are deposited. The absorbant medium is saturated with the impregnation solution in the preparation of the indicator and dried. Upon immersion for test purposes the absorbant medium picks up substantially the same amount of liquid and generates a solution of substantially the same concentration as the impregnating solution.

Where chromotography paper is the absorbant medium it takes up about 35 micro liters of impregnating solution per square centimeter of paper. After drying and when used in tests the paper takes up about 35 micro liters of glutaraldehyde solution, thereby generating a solution of the same concentration of the indicator system; i.e., sulfite and amino acid or ammonium compound. In gram quantities the amount of amino acid deposited on chromatography paper at solution concentrations of 0.1M to 0.3M are about $1 \times 10^{-4}$ to about $1 \times 10^{-3}$ grams.

Where the quantity of dry compound on the absorbant medium is referred to in terms of molar concentrations, that reference is to the amount which would be deposited on the absorbant medium by saturating the absorbant medium with a solution of the designated concentration.

It is known that the immersion time for disinfecting or sterilizing with and AGS is dependent on the pH of the AGS. Hence, in addition to knowing whether the concentration of glutaraldehyde in the AGS is 1% or greater, the pH of the AGS must be known. This measurement can be made using any suitable pH paper. For convenience the pH paper may be mounted on the backing strip along with the indicator of this invention. This indicator and pH paper may be mounted side by side on the backing strip, at opposite ends of the strip or on the same end with the pH indicator on one side and the indicator on the other. In this latter case a suitable backing strip comprises a surlyn-mylar-surlyn sandwich.

Referring now to the FIG. I, a preferred embodiment of the indicator of this invention is shown. An indicator medium, 1, in the form of a pad made of a water wettable absorbant material is adhered to a backing strip, 2, made of plastic or other material of suitable stiffness to act as a handle for the indicator pad. Optionally of pH paper, 3, is adhered to the reverse side of the backing strip.

The pad may be adhered to the backing strip by adhesive or heat sealing. For example, a backing strip comprising a laminate of mylar and surlyn is heat sealed at one end with a strip of paper of suitable width by placing the paper in contact with the surlyn surface and heat is applied. The paper is then saturated with the impregnating solution and air dried. Mylar ® is a terphthalic acid-ethylene glycol polyester and surlyn ® is a carboxylic acid inomer.

In a preferred embodiment the absorbant medium is heat bonded to a plastic layer of surlyn/mylar, impregnated with indicator solution and air dried. Subsequently, this indicating material is adhesively bonded to a backing strip which is preferably a non-absorbant rigid body, e.g. polyester film.

It will be evident from this disclosure that the solutions themselves will act as glutaraldehyde indicators. For example, an indicator solution of 0.1M $Na_2SO_3$ and 0.2M glycine can be furnished in a measured amount in a vial. In order to test a glutaraldehyde solution for effectiveness, the operator need only add a measured amount of glutaraldehyde to the indicator solutions and observe the response obtained. Alternately, the dry chemicals, e.g. $Na_2SO_3$ and glycine, may be preweighed at the $Na_2SO_3$/glycine ratios of this invention, and placed in a vial. In order to test an AGS for effectiveness, the operator need only add a predetermined measured amount of AGS solution and observe the response. The amount of AGS solution utilized in sufficient so that the concentration of available glycine in the AGS is about 0.1M to about 0.3M, more preferably about 0.15M to about 0.25M e.g. 0.2M.

Of course neither the sulfite compound nor the amine compound of this invention used alone give a color response. Hence, the sulfite/amine compound composition of this invention is a synergistic combination.

What is claimed is:

1. A glutaraldehyde indicator solution comprising a solution of a sulfite compound and an amine compound wherein the amine compound is (1) an amino acid where the amino acid is lysine or glysine or (2) an ammonium compound; said sulfite and amine compounds being present in an amount effective to distinguish between glutaraldehyde solutions of different glutaraldehyde concentrations.

2. The indicator solution according to claim 1 wherein the sulfite and amine compounds are present at a molar ratio of sulfite to amine compound of about 2.5/1 to about 20/1.

3. The indicator solution according to claim 2 wherein the molar ratio of sulfite to amine compound is 5/1.

4. The indicator solution according to claim 1 wherein the concentration of amine compound in the solution is about 0.1M to about 0.3M.

5. The indicator solution according to claim 4 wherein the amine compound concentration is about 0.15M to about 0.25M.

6. The indicator solution according to claim 5 wherein the amine concentration is 0.2M.

7. The indicator solution according to claim 1 wherein the amine compound is glycine or lysine.

8. The indicator solution according to claim 1 wherein the amine compound is an ammonium compound.

9. The indicator solution according to claim 1 wherein the ammonium compound is ammonium chloride, ammonium bromide, ammonium bicarbonate, ammonium acetate or ammonium formate.

10. The indicator according to claim 2 wherein the sulfite to amine compound ratio is 5/1, the amine compound ia glycine, the sulfite is sodium sulfite and the concentration of glycine in the solutions is 0.2M.

11. A glutaraldehyde indicating composition comprising an intimate mixture of a sulfite compound and an amine compound wherein the amine compound is (1) an amino acid, where the amino acid is glycine or lysine, or (2) an ammonium compound; and wherein said sulfite and amine compounds are present in an amount effective to distinguish between glutaraldehyde solutions of different glutaraldehyde concentrations.

12. The composition according to claim 11 wherein the amine compound is an amino acid.

13. The compound according to claim 11 wherein the molar ratio of sulfite compound to amine compound is about 2.5/1 to about 20/1.

14. The composition according to claim 12 wherein the amino acid is glycine.

15. The composition according to claim 13 wherein the ratio is about 5/1.

16. The composition according to claim 11 wherein the sulfite compound is $Na_2SO_3$.

* * * * *